(12) United States Patent
Kitamura et al.

(10) Patent No.: US 7,777,081 B2
(45) Date of Patent: Aug. 17, 2010

(54) 4-(4-ALKYLCYCLOHEXYL)BENZALDEHYDE

(75) Inventors: Mitsuharu Kitamura, Okayama (JP); Junya Nishiuchi, Okayama (JP); Norio Fushimi, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 12/299,980

(22) PCT Filed: May 8, 2007

(86) PCT No.: PCT/JP2007/059508

§ 371 (c)(1), (2), (4) Date: Nov. 7, 2008

(87) PCT Pub. No.: WO2007/129707

PCT Pub. Date: Nov. 15, 2007

(65) Prior Publication Data

US 2009/0118547 A1    May 7, 2009

(30) Foreign Application Priority Data

| May 9, 2006 | (JP) | 2006-130155 |
| Jul. 4, 2006 | (JP) | 2006-184728 |
| Jul. 4, 2006 | (JP) | 2006-184729 |

(51) Int. Cl.
C07C 47/54 (2006.01)
C07C 45/49 (2006.01)

(52) U.S. Cl. .......... 568/425; 568/428; 568/439

(58) Field of Classification Search .......... 568/428, 568/425, 430
See application file for complete search history.

(56) References Cited

U.S. PATENT DOCUMENTS

| 4,325,830 A | 4/1982 | Sethofer |
| 4,460,794 A | 7/1984 | Fujiyama et al. |
| 5,395,840 A | 3/1995 | Muller et al. |

FOREIGN PATENT DOCUMENTS

| JP | 56-077231 | 6/1981 |
| JP | 56-164179 | 12/1981 |
| JP | 62-067049 | 3/1987 |
| JP | 03-141274 | 6/1991 |
| JP | 06-293741 | 10/1994 |
| JP | 07-041435 | 2/1995 |
| JP | 07-278548 | 10/1995 |
| JP | 09-100286 | 4/1997 |
| JP | 09-278687 | 10/1997 |
| JP | 11-071338 | 3/1999 |
| JP | 11-171816 | 6/1999 |
| JP | 2004-256490 | 9/2004 |

OTHER PUBLICATIONS

Booth et al., "Formylation and Acylation Reactions Catalysed by Trifluoromethanesulphonic Acid", Journal of the Chemical Society. Transactions, 1, (1), pp. 181-186, (1980).

Primary Examiner—Sikarl A Witherspoon
(74) Attorney, Agent, or Firm—Antonelli, Terry, Stout & Kraus, LLP.

(57) ABSTRACT

A process for effectively producing a 4-(4-alkylcyclohexyl) benzaldehyde, 4-(cyclohexyl)benzaldehyde, a 4-(trans-4-alkylcyclohexyl)benzaldehyde and a (trans-4-alkylcyclohexyl)benzene useful for electronic material applications such as liquid crystals and for pharmaceutical and agrochemical applications, etc., are disclosed. The present invention provides (1) a process for producing a 4-(4-alkylcyclohexyl) benzaldehyde or 4-(cyclohexyl)benzaldehyde by formylating a (4-alkylcyclohexyl)benzene or cyclohexylbenzene with carbon monoxide, (2) a process for producing a 4-(trans-4-alkylcyclohexyl)benzaldehyde by formylating a (4-alkylcyclohexyl)benzene having a cis/trans molar ratio of 0.3 or less with carbon monoxide, and (3) a process for producing a (trans-4-alkylcyclohexyl)benzene by isomerizing a mixture of the cis and trans isomers of a (4-alkylcyclohexyl)benzene, all of the processes being performed in the presence of HF and $BF_3$.

12 Claims, No Drawings

4-(4-ALKYLCYCLOHEXYL)BENZALDEHYDE

TECHNICAL FIELD

The present invention relates to a cyclohexylbenzene derivative such as a 4-(4-alkylcyclohexyl)benzaldehyde and to a process for producing the same. More particularly, the present invention relates to processes for producing a 4-(4-alkylcyclohexyl)benzaldehyde, 4-(cyclohexyl)-benzaldehyde, a 4-(trans-4-alkylcyclohexyl)benzaldehyde and a (trans-4-alkylcyclohexyl)benzene which can be suitably used for functional chemicals such as those for electronic material applications inclusive of liquid crystals and for pharmaceutical and agrochemical applications.

BACKGROUND ART

Cyclohexylbenzene derivatives are known as liquid crystal compounds (refer to Non-Patent Document 1). For example, a process for producing 4-(trans-4-heptylcyclohexyl)benzoic acid is disclosed (refer to Patent Document 1) and 4'-(4-propylhexyl)biphenyl-4-yl-acetate is disclosed (refer to Patent Document 2). Further, 4-(trans-4-pentylcyclohexyl) benzaldehyde (refer to Non-Patent Document 2), 4-(trans-4-proylcyclohexyl)benzaldehyde (refer to Patent Document 3), etc., are used. On the other hand, as a photopolymerization initiator, 1,2-bis(4-(4-propylcyclohexyl)phenyl)ethane-1,2-dione is disclosed (refer to Patent Document 4). Cyclohexylbenzene derivatives are also used in pharmaceutical applications and are understood to have a possibility to be used as functional materials in a variety of fields (refer to Patent Document 5).

Thus, cyclohexylbenzene derivatives are developed mainly for use as liquid crystal compounds and, additionally, have a possibility to be applied and developed in various fields such as those of pharmaceuticals and functional materials. In this circumstance, development of novel compounds is positively attempted.

In such technologies, a process for producing 4-(trans-4-pentylcyclohexyl)benzaldehyde by oxidation of 4-(trans-4-pentylcyclohexyl)benzyl alcohol with chromic acid is known (refer to Non-Patent Document 2). The known process is, however, not preferable as an industrial method, because 4-(trans-4-pentylcyclohexyl)benzyl alcohol as the raw material is not easily available and because chromic acid which is strongly toxic must be used. A process for producing 4-(trans-4-propylcyclohexyl)benzaldehyde by reducing 4-(trans-4-propylcyclohexyl)benzonitrile with NaAlH$_2$(OC$_2$H$_4$OCH$_3$)$_2$ is also known (refer to Patent Document 3). This process is also problematic as an industrial method, because 4-(trans-4-propylcyclohexyl)benzonitrile as the raw material is not easily available, because a large amount of the expensive NaAlH$_2$(OC$_2$H$_4$OCH$_3$)$_2$ must be used as a reducing agent, and because wastes such as Al(OH)$_3$ are by-produced in a large amount.

A 4-(4-alkylcyclohexyl)benzaldehyde may also be produced from a (4-alkylcyclohexyl)benzene as follows. A (4-alkylcyclohexyl)benzene is first reacted with bromine in the presence of a reduced iron catalyst to obtain a 4-(4-alkylcyclohexyl)bromobenzene. Then, an ether solution of the refined 4-(4-alkylcyclohexyl)bromobenzene is added dropwise to an ether solution containing metallic magnesium. The resulting mixture is reacted with ethyl orthoformate to obtain a 4-(4-alkylcyclohexyl)benzaldehyde diethylacetal, which is finally hydrolyzed with an aqueous hydrochloric acid solution to obtain the 4-(4-alkylcyclohexyl)-benzaldehyde as aimed.

In addition to the desired trans isomer, however, the thus obtained aldehyde product tends to contain the cis isomer in an amount corresponding to that in the raw material. Because the boiling points of these isomers are very close to each other, it is impossible to separate and purify them by distillation. It may be considered that the trans-isomer is isolated by a crystallization method. Such a method is, however, not efficient and incurs a high cost. Thus, there is a demand for an effective method for selectively producing the trans isomer by controlling the reaction conditions.

In general, a cyclohexylbenzene derivative is produced as a mixture of the cis and trans isomers thereof. Therefore, it is necessary to adopt a method for separating the trans isomer from the mixture. As a method for separating the trans isomer from the isomeric mixture, a crystallization method is generally used as mentioned above. Such a method is, however, not efficient and incurs a high cost.

A method for efficiently producing the trans isomer by isomerization of the cis isomer into the trans isomer is also investigated. For example, Patent Document 6 and Patent Document 7 disclose a method of obtaining the trans isomer by isomerizing the cis isomer into the trans isomer using potassium t-butoxide. This method, however, must use a large amount of potassium t-butoxide and, therefore, has a problem that a treatment of an alkali waste liquor remaining after the reaction causes a great work load.

There is also disclosed a method in which a cis isomer is isomerized into a trans isomer in the presence of a Lewis acid, such as aluminum chloride, and an alkyl halide compound (refer to Patent Document 8). This method, however, poses a problem of treatment of aluminum chloride after the reaction and, additionally, must use a solvent such as methylene chloride which has high environment load.

Further, a method for isomerizing a cis isomer into a trans isomer using a hetero-polyacid is disclosed (refer to Patent Document 9). This method, however, requires a long reaction time and does not necessarily provide a high reaction efficiency.

Further, a method for isomerizing a cis isomer into a trans isomer using trifluoromethanesulfonic acid is disclosed (refer to Patent Document 10). This method is, however, not economical because a large amount of expensive trifluoromethanesulfonic acid must be used and, additionally, has a problem that methylene chloride which has high environment load must be used as an extraction solvent.

Non-Patent Document 1: Quarterly Chemical Review 22, "Chemistry of Liquid Crystals", Yasuyuki GOTO, published by Academy Publication Center, Apr. 25, 1994, p. 40-59

Non-Patent Document 2: HELVETICA CHIMICA ACTA, Vol. 68 (1985), p. 1444-1452

Patent Document 1: Japanese Patent Application Laid-Open No. S56-077231

Patent Document 2: Japanese Patent Application Laid-Open No. S62-067049

Patent Document 3: Japanese Patent Application Laid-Open No. H03-141274

Patent Document 4: Japanese Patent Application Laid-Open No. H11-171816

Patent Document 5: Japanese Patent Application Laid-Open No. H06-293741

Patent Document 6: Japanese Patent Application Laid-Open No. H07-278548

Patent Document 7: Japanese Patent Application Laid-Open No. H09-278687

Patent Document 8: Japanese Patent Application Laid-Open No. H09-100286

Patent Document 9: Japanese Patent Application Laid-Open No. H07-41432

Patent Document 10: Japanese Patent Application Laid-Open (KOKAI) No. 2004-256490

DISCLOSURE OF THE INVENTION

Problems to be Solved by the Invention

In view of such circumstance, a first object of the present invention is to provide a process for producing a 4-(4-alkylcyclohexyl)benzaldehyde or 4-(cyclohexyl)benzaldehyde which can be suitably used for functional chemicals such as those for electronic material applications inclusive of liquid crystals and for pharmaceutical and agrochemical applications, and a novel 4-(4-alkylcyclohexyl)benzaldehyde. A second object of the present invention is to provide an industrial production process which is capable of selectively synthesizing a 4-(trans-4-alkylcyclohexyl)benzaldehyde, and permitting high purity products to be easily obtained. A third object of the present invention is to provide an industrial production process which is capable of selectively synthesizing a (trans-4-alkylcyclohexyl)benzene, which can be suitably used for functional chemicals such as those for electronic material applications inclusive of liquid crystals and for pharmaceutical and agrochemical applications, and permitting high purity products to be easily obtained.

Means for Solving the Problems

As a result of an earnest study for solving the above problems, the present inventors have found that the above first object of the present invention can be achieved by formylating a (4-alkylcyclohexyl)benzene or cyclohexylbenzene with carbon monoxide in the copresence of hydrogen fluoride (hereinafter occasionally referred to as HF) and boron trifluoride (hereinafter occasionally referred to as $BF_3$), and that the second object of the present invention can be achieved by formylating a (4-alkylcyclohexyl)benzene having a cis/trans ratio of not greater than a specific value with carbon monoxide in the copresence of HF—$BF_3$. Further, it has been found that the third object of the present invention can be achieved by isomerizing a mixture of the cis and trans isomers of a (4-alkylcyclohexyl)benzene in the copresence of HF—$BF_3$. The present invention has been accomplished on the basis of the above findings.

That is, the present invention provides as follows:

[1] A process for producing a 4-(4-alkylcyclohexyl)-benzaldehyde or 4-(cyclohexyl)benzaldehyde, comprising formylating a benzene derivative represented by the following formula (1a) with carbon monoxide in the presence of hydrogen fluoride and boron trifluoride to obtain a 4-(4-alkylcyclohexyl)benzaldehyde or 4-(cyclohexyl)benzaldehyde represented by the following formula (2).

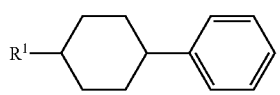

In the formula (1a), $R^1$ represents an alkyl group having 1 to 10 carbon atoms, or a hydrogen atom.

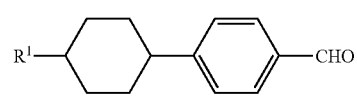

In the formula (2), $R^1$ represents an alkyl group having 1 to 10 carbon atoms, or a hydrogen atom.

[2] 4-(4-n-Butylcyclohexyl)benzaldehyde represented by the following formula (3).

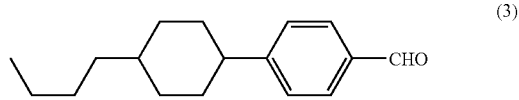

[3] A process for producing a 4-(trans-4-alkylcyclohexyl)benzaldehyde, comprising formylating a (4-alkylcyclohexyl)benzene represented by the following formula (1b) and having a cis/trans molar ratio of 0.3 or less with carbon monoxide in the presence of hydrogen fluoride and boron trifluoride to obtain a 4-(trans-4-alkylcyclohexyl)benzaldehyde represented by the following formula (4).

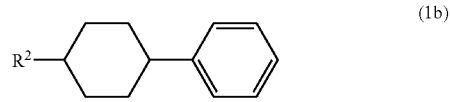

In the formula (1b), $R^2$ represents an alkyl group having 1 to 10 carbon atoms.

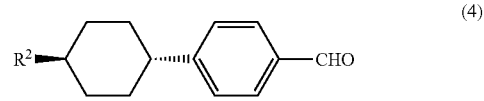

In the formula (4), $R^2$ represents an alkyl group having 1 to 10 carbon atoms.

[4] A 4-(trans-4-alkylcyclohexyl)benzaldehyde having a purity of the 4-(4-alkylcyclohexyl)benzaldehyde of 98% or more and a purity of the trans-isomer of 99% or more.

[5] A process for producing a (trans-4-alkylcyclohexyl)benzene represented by the following formula (5), comprising isomerizing a mixture of the cis and trans isomers of a (4-alkylcyclohexyl)benzene represented by the above formula (1b) in the presence of hydrogen fluoride and boron trifluoride.

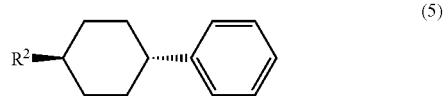

In the formula (5), $R^2$ represents an alkyl group having 1 to 10 carbon atoms.

[6] A process for producing a 4-(trans-4-alkylcyclohexyl)benzaldehyde, comprising isomerizing a mixture of the cis and trans isomers of a (4-alkylcyclohexyl)benzene represented by the above formula (1b) in the presence of hydrogen fluoride and boron trifluoride to obtain a (trans-4-alkylcyclohexyl)benzene represented by the above formula (5), and then successively formylating the (trans-4-alkylcyclohexyl)benzene with carbon monoxide to obtain a 4-(trans-4-alkylcyclohexyl)benzaldehyde represented by the above formula (4).

EFFECT OF THE INVENTION

According to the process of the present invention, a 4-(4-alkylcyclohexyl)benzaldehyde or 4-(cyclohexyl)benzaldehyde, which can be suitably used for functional chemicals such as those for electronic material applications inclusive of liquid crystals and for pharmaceutical and agrochemical applications, can be produced with a good efficiency by formylating a (4-alkylcyclohexyl)benzene or cyclohexylbenzene with carbon monoxide in the copresence of HF—BF$_3$. 4-(4-n-Butylcyclohexyl)benzaldehyde obtained by the above process is a novel compound and is a useful compound for electronic material applications such as liquid crystals and for pharmaceutical and agrochemical applications.

Further, according to the process of the present invention, a 4-(trans-4-alkylcyclohexyl)benzaldehyde can be selectively easily produced by reacting a (4-alkylcyclohexyl)benzene with carbon monoxide in the copresence of HF—BF$_3$.

Further, according to the process of the present invention, a high purity (trans-4-alkylcyclohexyl)benzene can be selectively easily produced by isomerizing a mixture of the cis and trans isomers of a (4-alkylcyclohexyl)benzene in the copresence of HF—BF$_3$. This compound is a useful compound, for example, for electronic material applications such as liquid crystals and for pharmaceutical and agrochemical applications.

PREFERRED EMBODIMENTS FOR CARRYING OUT THE INVENTION

The process for producing a 4-(4-alkylcyclohexyl)-benzaldehyde according to the present invention is characterized in that a benzene derivative represented by the following formula (1a) is formylated with carbon monoxide in the presence of HF and BF$_3$ to obtain a 4-(4-alkylcyclohexyl)benzaldehyde represented by the following formula (2).

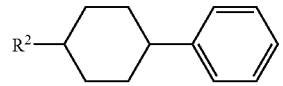
(1a)

In the formula (1a), R$^1$ represents an alkyl group having 1 to 10 carbon atoms, or a hydrogen atom.

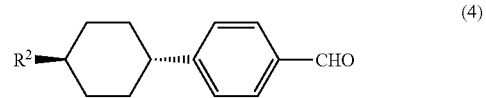
(2)

In the formula (2), R$^1$ represents an alkyl group having 1 to 10 carbon atoms, or a hydrogen atom.

The process for producing a 4-(trans-4-alkylcyclohexyl) benzaldehyde according to the present invention is characterized in that a (4-alkylcyclohexyl)benzene represented by the following formula (1b) which has a cis/trans molar ratio of 0.3 or less is formylated with carbon monoxide in the presence of HF and BF$_3$ to obtain a 4-(trans-4-alkylcyclohexyl)benzaldehyde represented by the following formula (4).

(1b)

In the formula (1b), R$^2$ represents an alkyl group having 1 to 10 carbon atoms.

(4)

In the formula (4), R$^2$ represents an alkyl group having 1 to 10 carbon atoms.

Examples of the alkyl group having 1 to 10 carbon atoms which is represented by R$^1$ in the formula (1a) or by R$^2$ in the formula (1b), include a methyl group, an ethyl group, an n-propyl group, an isopropyl group, an n-butyl group, a sec-butyl group, a tert-butyl group, an n-pentyl group, an n-hexyl group, an n-heptyl group, an n-octyl group, an n-nonyl group and an n-decyl group. Among these groups, preferred are a methyl group, an ethyl group, an n-propyl group, an n-butyl group, an n-pentyl group, an n-hexyl group and an n-heptyl group, and more preferred are an n-propyl group, an n-butyl group and an n-pentyl group.

The benzene derivative represented by the formula (1a) or (1b) may be produced in accordance with a method described in Journal of Organic Chemistry of the USSR, vol. 19, p. 1479-1483, 1983. Namely, raw materials including cyclohexene, a fatty acid chloride and benzene are reacted in the copresence of AlCl$_3$, and the obtained 4-alkanoyl-1-phenylcyclohexane is then subjected to Wolf-Kishner reduction. Alternatively, the benzene derivative may be produced by a method disclosed in Japanese Patent Application Laid-Open No. H09-100286, in which a Grignard reagent prepared from bromobenzene and magnesium is reacted with a 4-alkylcyclohexanone, followed by dehydration and hydrogenation.

A (4-alkylcyclohexyl)benzene of the formula (1b) has two kinds of isomers, i.e., trans and cis isomers. In the production of 4-(trans-4-alkylcyclohexyl)benzaldehyde represented by the formula (4), the (4-alkylcyclohexyl)benzene preferably has a cis/trans molar ratio of 0.3 or less, more preferably 0.1 or less. A cis/trans molar ratio of 0.3 or less is preferred, since the purity of the produced 4-(trans-4-alkylcyclohexyl)benzaldehyde (hereinafter occasionally referred to as "trans isomer purity") is 99% or more while the purity of the produced 4-(cis-4-alkylcyclohexyl)benzaldehyde (hereinafter occasionally referred to as "cis isomer purity") is 1% or less. When it is necessary to further increase the trans isomer purity, the cis/trans molar ratio is preferably 0.08 or less, more preferably 0.05 or less for the same reasons as described above. As used herein, the term "trans isomer purity" is intended to refer to a proportion (%) of the trans isomer on the basis of a total amount of the trans and cis isomers, while the term "cis isomer purity" is intended to refer to a proportion (%) of the cis isomer based on a total amount of the trans and cis isomers.

The cis/trans ratio may be analyzed by gas chromatography. As a method for producing a (4-alkylcyclohexyl)benzene having a cis/trans molar ratio of 0.3 or less, there may be used, for example, a method in which a 4-alkanoyl-1-phenylcyclohexane produced by the above method or a (4-alkylcyclohexyl)benzene is crystallized using a suitable solvent.

In the present invention, it is particularly important that the benzene derivative represented by the formula (1a) or (1b) is reacted with carbon monoxide using, as a catalyst, HF and $BF_3$ in order to produce a 4-(4-alkylcyclohexyl)benzaldehyde or 4-(cyclohexyl)benzaldehyde represented by the formula (2), or a 4-(trans-4-alkylcyclohexyl)benzaldehyde represented by the formula (4). When such a production process is adopted, it is possible to selectively formylate the p-position on the benzene ring relative to the cyclohexyl group and to obtain the desired 4-(4-alkylcyclohexyl)benzaldehyde or 4-(cyclohexyl)benzaldehyde represented by the formula (2), or 4-(trans-4-alkylcyclohexyl)benzaldehyde represented by the formula (4). Since HF and $BF_3$ used as a catalyst are highly volatile, they can be recovered and recycled. Thus, it is not necessary to discard the used catalyst. Accordingly, the process is economically excellent and can reduce environment load.

It is preferred that HF used in the process of the present invention be substantially anhydrous. The amount of HF used relative to the benzene derivative of the formula (1a) or (1b) is preferably in the range of 2 to 30 moles, more preferably 3 to 20 moles, per 1 mole of the benzene derivative of the formula (1a) or (1b). When the amount of HF used is less than the above-specified range, the formylation cannot efficiently proceed. Too large an amount of HF in excess of the above-specified range is not preferable from the viewpoint of production efficiency because a large-size reactor tends to be required, and an HF recovering work load tends to be increased. The amount of $BF_3$ used relative to the benzene derivative of the formula (1a) or (1b) is preferably in the range of 1 to 10 moles, more preferably 1.1 to 5 moles, per 1 mole of the benzene derivative of the formula (1a) or (1b). When the amount of $BF_3$ used is less than the above-specified range, the formylation rate tends to become extremely slow and the selectivity for the p-position tends to become poor. When the amount of $BF_3$ used is more than the above-specified range, the partial pressure of $BF_3$ tends to be increased, and the partial pressure of carbon monoxide tends to be reduced, resulting in poor yield.

The formylation in the present invention is preferably carried out at a temperature of from −50° C. to 30° C., more preferably from −30° C. to 20° C. At a reaction temperature higher than the above-specified range, significant side reactions, such as decomposition and polymerization, of the benzene derivative represented by the formula (1a) or (1b), 4-(4-alkylcyclohexyl)benzaldehyde or 4-(cyclohexyl)benzaldehyde represented by the formula (2), or 4-(trans-4-alkylcyclohexyl)benzaldehyde represented by the formula (4) tend to occur. A reaction temperature lower than the above-specified range is not preferable because the formylation rate tends to become slow.

The pressure of carbon monoxide in the formylation is preferably 0.5 to 3 MPa, more preferably 0.7 to 3 MPa, from the standpoint of the yield. A pressure of more than 3 MPa is economically disadvantageous and is unnecessary.

The formylation of a benzene derivative represented by the formula (1a) or (1b) with carbon monoxide in the copresence of HF and $BF_3$ may be carried out with or without a solvent. The solvent used is preferably inert to the reaction and is, for example, an aliphatic hydrocarbon such as n-hexane or n-heptane. When a solvent is used, the amount thereof is preferably 0.5 to 20 parts by mass per part by mass of the benzene derivative represented by the formula (1a) or (1b).

A type of the reaction for carrying out the formylation in the present invention is not particularly restricted as long as it permits stirring for sufficiently mixing a liquid phase and a gas phase. Thus, any of a batch method, a semi-batch method, a continuous method, etc., may be used.

In the case of a batch method, for example, a benzene derivative represented by the formula (1a) or (1b), anhydrous HF and $BF_3$ are charged in an autoclave equipped with an electromagnetic stirrer. The contents are maintained at a liquid temperature of about −50° C. to 30° C. with stirring. The pressure is increased to about 0.5 to 3 MPa using carbon monoxide. Then, carbon monoxide is fed while maintaining the autoclave at that pressure and at that liquid temperature. The mixture is maintained as such until carbon monoxide is no longer absorbed. The contents in the autoclave were poured onto ice to obtain an oil layer. The formation of 4-(4-alkylcyclohexyl)benzaldehyde or 4-(cyclohexyl)benzaldehyde represented by the formula (2), or 4-(trans-4-alkylcyclohexyl)benzaldehyde represented by the formula (4) may be confirmed by analyzing the oil layer by gas chromatography.

In the case of a semi-batch method, for example, anhydrous HF and $BF_3$ are charged in an autoclave equipped with an electromagnetic stirrer. The contents are set at a liquid temperature of about −50° C. to 30° C. with stirring. The autoclave is controlled so that the liquid temperature is maintained at constant. The pressure is increased to about 0.5 to 3 MPa using carbon monoxide. The autoclave is controlled so that carbon monoxide may be fed while maintaining the autoclave at that pressure. Then, a benzene derivative of the formula (1a) or (1b) dissolved in a solvent is fed to the autoclave. After completion of feeding the raw material, the autoclave is maintained as such for a predetermined period of time. The contents in the autoclave were poured onto ice to obtain an oil layer. The formation of 4-(4-alkylcyclohexyl)benzaldehyde or 4-(cyclohexyl)benzaldehyde represented by the formula (2), or 4-(trans-4-alkylcyclohexyl)benzaldehyde represented by the formula (4) may be confirmed by analyzing the oil layer by gas chromatography.

In the case of a continuous method, for example, anhydrous HF and $BF_3$ are first charged in an autoclave equipped with an electromagnetic stirrer. The contents are set at a liquid temperature of about −50° C. to 30° C. with stirring. The autoclave is controlled so that the liquid temperature is maintained at constant. The pressure is increased to about 0.5 to 3 MPa using carbon monoxide. The autoclave is controlled so that carbon monoxide may be fed while maintaining the autoclave at that pressure. Then, a benzene derivative of the formula (1a) or (1b) dissolved in a solvent is fed to the autoclave to conduct the reaction by a semi-batch method. Successively, anhydrous HF and $BF_3$ are started to feed, while continuously discharging the reaction liquid into ice water. The residence time of the reaction liquid in the autoclave is preferably 1 to 5 h. When the residence time is shorter than the above-specified range, the reaction tends to fail to sufficiently proceed. Too long a residence time in excess of the above-specified range results in poor efficiency because it is necessary to use a large apparatus. The formation of 4-(4-alkylcyclohexyl)benzaldehyde or 4-(cyclohexyl)benzaldehyde represented by the formula (2), or 4-(trans-4-alkylcyclohexyl)benzaldehyde represented by the formula (4) may be confirmed by analyzing an obtained oil layer by gas chromatography.

The endpoint of the reaction is not specifically defined, but may be, for example, the point in time at which the absorption of carbon monoxide is stopped.

The reaction product liquid obtained by the formylation is an HF solution of a 4-(4-alkylcyclohexyl)benzaldehyde.HF—$BF_3$ complex, an HF solution of a 4-(cyclohexyl)benzaldehyde.HF—$BF_3$ complex, or an HF solution of a 4-(trans-4-alkylcyclohexyl)benzaldehyde.HF—BF₃ complex. When the complex is heated, the bond between HF—BF₃ and 4-(4-alkylcyclohexyl)benzaldehyde, 4-(cyclohexyl)benzaldehyde or 4-(trans-4-alkylcyclohexyl)benzaldehyde is decomposed. Thus, HF and BF₃ are separated by vaporization from the solution and, therefore, can be recovered and recycled. In this case, it is necessary to decompose the complex as rapidly as possible and to avoid thermal deterioration and isomerization of the product. In order to rapidly decompose the complex, it is desirable to perform the decomposition under reflux of a solvent inert to HF—BF₃ (for example, a saturated hydrocarbon such as heptane or an aromatic hydrocarbon such as benzene).

The present invention also provides 4-(4-n-butylcyclohexyl)benzaldehyde represented by the following formula (3).

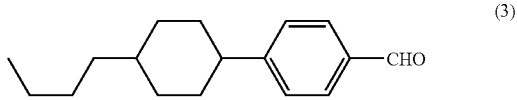

(3)

4-(4-n-Butylcyclohexyl)benzaldehyde of the formula (3), which is a novel compound, may be prepared by reacting (4-n-butylcyclohexyl)benzene, used as a (4-alkylcyclohexyl)benzene, with carbon monoxide in the copresence of HF and BF₃ in the same manner as described above.

The present invention further provides a 4-(trans-4-alkylcyclohexyl)benzaldehyde having a purity of the 4-(4-alkylcyclohexyl)benzaldehyde of 98% or more and a purity of the trans-isomer of 99% or more.

This substance may be easily obtained by refining by distillation a crude product obtained by the thermal decomposition of an HF solution of a 4-(trans-4-alkylcyclohexyl)benzaldehyde.HF—BF₃ complex.

A cyclic polyphenol compound may be synthesized using, as raw materials, a 4-(4-alkylcyclohexyl)benzaldehyde obtained by the production process of the present invention and a phenol compound by subjecting these compounds to dehydrative condensation in the presence of an acid catalyst. The cyclic polyphenol compound may be used for an undercoat layer-forming composition useful in a multilayer resist coating step in a micropatterning process for the fabrication of semiconductor devices or the like.

A process for producing a (trans-4-alkylcyclohexyl)benzene according to the present invention comprises isomerizing a mixture of the cis and trans isomers of a (4-alkylcyclohexyl)benzene represented by the above formula (1b) in the presence of HF and BF₃ to obtain a (trans-4-alkylcyclohexyl)benzene represented by the following formula (5).

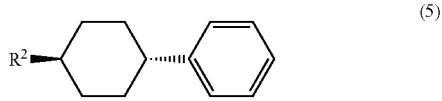

(5)

In the formula (5), R² represents an alkyl group having 1 to 10 carbon atoms.

In the present invention, it is particularly important that the cis isomer contained in a (trans-4-alkylcyclohexyl)benzene represented by the formula (1b) is isomerized into the trans isomer using, as a catalyst, HF and BF₃ in order to produce a (trans-4-alkylcyclohexyl)benzene represented by the formula (5). When such a production process is adopted, it is possible to obtain the aimed (trans-4-alkylcyclohexyl)benzene represented by the formula (5). Since HF and BF₃ used as a catalyst are highly volatile, they can be recovered and recycled. Thus, it is not necessary to discard the used catalyst. Accordingly, the process is economically very excellent and can reduce environment load.

The mixture of the cis and trans isomers of a (4-alkylcyclohexyl)benzene used in the present invention may be prepared by a method described in Journal of Organic Chemistry of the USSR, vol. 19, p. 1479-1483, 1983, a method disclosed in Japanese Patent Application Laid-Open No. H09-100286, or a method disclosed in Japanese Patent Application Laid-Open No. H07-278548. The cis/trans molar ratio of the (4-alkylcyclohexyl)benzene is 0.3 or more.

It is preferred that HF used in the process of the present invention be substantially anhydrous. The amount of HF used relative to the mixture of the cis and trans isomers of the (4-alkylcyclohexyl)benzene of the formula (1b) is preferably in the range of 2 to 30 moles, more preferably 2 to 20 moles, per 1 mole of the mixture of the cis and trans isomers of the (4-alkylcyclohexyl)benzene of the formula (1b). When the amount of HF used is less than the above-specified range, the isomerization tends to fail to efficiently proceed. Too large an amount of HF in excess of the above-specified range is not preferable from the viewpoint of production efficiency because a large-size reactor tends to be required, and an HF recovering work load tends to be increased. The amount of BF₃ used relative to the mixture of the cis and trans isomers of the (4-alkylcyclohexyl)benzene of the formula (1b) is preferably in the range of 0.1 to 2 moles, more preferably 0.1 to 1 mole, per 1 mole of the mixture of the cis and trans isomers of the (4-alkylcyclohexyl)benzene of the formula (1b). When the amount of BF₃ used is less than the above-specified range, the isomerization rate tends to become extremely slow. It is unnecessary to use BF₃ in excess of the above-specified range.

The isomerization reaction in the present invention is preferably carried out at a temperature of from −50° C. to 30° C., more preferably from −30° C. to 20° C. At a reaction temperature higher than the above-specified range, side reactions, such as decomposition, of the mixture of the cis and trans isomers of the (4-alkylcyclohexyl)benzene of the formula (1b), or (trans-4-alkylcyclohexyl)benzene represented by the formula (5) tend to occur. A reaction temperature lower than the above-specified range is not preferable because the isomerization rate tends to become slow.

The isomerization of a mixture of the cis and trans isomers of the (4-alkylcyclohexyl)benzene of the formula (1b) in the copresence of HF and BF₃ may be carried out with or without a solvent. The solvent used is preferably inert to the reaction and is, for example, an aliphatic hydrocarbon such as n-hexane or n-heptane. When a solvent is used, the amount thereof is preferably 0.5 to 20 parts by mass per part by mass of the mixture of the cis and trans isomers of the (4-alkylcyclohexyl)benzene of the formula (1b).

A type of the reaction for carrying out the isomerization in the process of the present invention is not particularly restricted as long as it permits stirring for sufficiently mixing a liquid phase and a gas phase. Thus, any of a batch method, a semi-batch method, a continuous method, etc., may be used.

In the case of a batch method, for example, a mixture of the cis and trans isomers of the (4-alkylcyclohexyl)benzene of the formula (1b), anhydrous HF and BF₃ are charged in an autoclave equipped with an electromagnetic stirrer. The contents are maintained at a liquid temperature of −50° C. to 30° C. with stirring and thereafter poured onto ice to obtain an oil layer. The formation of (trans-4-alkylcyclohexyl)benzene represented by the formula (5) may be confirmed by analyzing the oil layer by gas chromatography.

In the case of a semi-batch method, for example, anhydrous HF and $BF_3$ are charged in an autoclave equipped with an electromagnetic stirrer. The contents are set at a liquid temperature of −50° C. to 30° C. with stirring. The autoclave is controlled so that the temperature is maintained at constant. Then, a mixture of the cis and trans isomers of the (4-alkylcyclohexyl)benzene of the formula (1b) dissolved in a solvent is fed to the autoclave. After completion of feeding the raw material, the autoclave is maintained as such for a predetermined period of time. The contents in the autoclave were poured onto ice to obtain an oil layer. The formation of (trans-4-alkylcyclohexyl)benzene represented by the formula (5) may be confirmed by analyzing the obtained oil layer by gas chromatography.

In the case of a continuous method, for example, anhydrous HF and $BF_3$ are first charged in an autoclave equipped with an electromagnetic stirrer. The contents are set at a liquid temperature of −50° C. to 30° C. with stirring. The autoclave is controlled so that the liquid temperature is maintained at constant. Then, a mixture of the cis and trans isomers of the (4-alkylcyclohexyl)benzene is fed to the autoclave to conduct the reaction by a semi-batch method. Successively, anhydrous HF and $BF_3$ are also started to feed, while continuously discharging the reaction liquid into ice water. The residence time of the reaction liquid in the autoclave is preferably 0.3 to 5 h. When the residence time is shorter than the above-specified range, the reaction tends to fail to sufficiently proceed. Too long a residence time in excess of the above-specified range results in poor efficiency because it is necessary to use a large apparatus. The formation of (trans-4-alkylcyclohexyl)benzene represented by the formula (5) may be confirmed by analyzing the obtained oil layer by gas chromatography.

The reaction product liquid obtained by the isomerization is an HF solution of a (trans-4-alkylcyclohexyl)benzene.HF—$BF_3$ complex. When the complex is heated, the bond between (trans-4-alkylcyclohexyl)benzene and HF—$BF_3$ is decomposed. Thus, HF and $BF_3$ are separated by vaporization from the solution and, therefore, can be recovered and recycled. In this case, it is necessary to perform the decomposition of the complex as rapidly as possible and to avoid thermal deterioration and isomerization of the product. In order to rapidly decompose the complex, it is desirable to perform the decomposition under reflux of a solvent inert to HF—$BF_3$ (for example, a saturated hydrocarbon such as heptane or an aromatic hydrocarbon such as benzene). The crude product obtained by the thermal decomposition can be easily purified by distillation to obtain a (trans-4-alkylcyclohexyl) benzene having a cis/trans molar ratio of less than 0.1.

The thus obtained (trans-4-alkylcyclohexyl)benzene can be used as a raw material for the production of a 4-(trans-4-alkylcyclohexyl)benzaldehyde of the above formula (4).

The present invention further provides a process for producing a 4-(trans-4-alkylcyclohexyl)benzaldehyde, comprising isomerizing a mixture of the cis and trans isomers of a (4-alkylcyclohexyl)benzene represented by the above formula (1b) in the presence of HF and $BF_3$ to obtain a (trans-4-alkylcyclohexyl)benzene represented by the above formula (5), and then successively formylating the (trans-4-alkylcyclohexyl)benzene with carbon monoxide to obtain a 4-(trans-4-alkylcyclohexyl)benzaldehyde represented by the above formula (4).

In this production process, both the isomerization and the succeeding formylation may be carried out in the presence of the same HF and $BF_3$.

In the isomerization, the amounts of HF and $BF_3$ used relative to the mixture of the cis and trans isomers of a (4-alkylcyclohexyl)benzene represented by the above formula (1b) may be the same as those in the previously described isomerization.

The formylation reaction is carried out by feeding carbon monoxide and an additional amount of $BF_3$ for compensating its deficiency to the isomerization reaction liquid. The total amount of $BF_3$ inclusive of the additional amount thereof relative to the mixture of the cis and trans isomers of a (4-alkylcyclohexyl)benzene represented by the above formula (1b) may be the same as that in the previously described formylation.

EXAMPLES

The present invention will be described in more detail below by the following examples. It should be noted, however, that the following examples are only illustrative and not intended to limit the invention thereto.

Synthesis Example 1

Synthesis of (4-n-propylcyclohexyl)benzene
(Cis/Trans Molar Ratio: 1.36)

In a 2,000 mL (inside volume) three-necked flask equipped with a reflux condenser, 600 mL of hexane and 160 g of anhydrous $AlCl_3$ were mixed and cooled to −60° C., to which were then added 110 g of propionyl chloride and 82.2 g of cyclohexene. The temperature of the mixture was raised to −40° C. while stirring the mixture for 3.5 h. The solvent was then removed by decantation and the residues were washed with cold hexane. The thus obtained 1-propionyl-2-chlorocyclohexane was added with 500 mL of benzene and an additional amount (60 g) of $AlCl_3$. The mixture was then stirred at 45° C. for 3.5 h. The reaction liquid was cooled to room temperature and then poured onto ice. An oil layer was separated and concentrated to obtain 130 g of (4-propionylcyclohexyl)benzene. This was mixed with 1,200 mL of diethylene glycol, 225 g of potassium hydroxide and 310 g of 80% by mass hydrazine hydrate. After refluxing the resulting mixture for 1 h, the contents in the flask were heated to 220° C. to distil off volatile matters therefrom. The mixture was further refluxed for 1 h, cooled to room temperature and then poured in water. An oil layer was then extracted with hexane, washed with water, 5% by mass sulfuric acid and 80% by mass sulfuric acid and then dried. The obtained oil layer was purified by distillation to obtain 85 g of (4-n-propylcyclohexyl)benzene. As a result of gas chromatography, it was confirmed that the (4-n-propylcyclohexyl)benzene purity was 98.0% and the cis/trans molar ratio was 1.36.

Synthesis Example 2

Synthesis of (4-n-propylcyclohexyl)benzene
(Cis/Trans Molar Ratio: 0.05)

In 50 g of hexane were dissolved 100 g of (4-n-propylcyclohexyl)benzene obtained in Synthesis Example 1 at 50° C. The resulting solution was cooled to −30° C. Precipitated crystals were collected by filtration in an amount of 35 g. The crystals were mixed with 300 mL of diethylene glycol, 60 g of potassium hydroxide and 80 g of 80% by mass hydrazine hydrate. After refluxing the resulting mixture for 1 h, the contents in the flask were heated to 220° C. to distil off volatile matters therefrom. The mixture was further refluxed for 1 h, cooled to room temperature and then poured in water. An oil layer was then extracted with hexane, washed with water, 5% by mass sulfuric acid and 80% by mass sulfuric acid and then dried. The obtained oil layer was purified by distillation to obtain 26 g of (4-n-propylcyclohexyl)benzene. As a result of gas chromatography, it was confirmed that the (4-n-propylcyclohexyl)benzene purity was 98.0% and the cis/trans molar ratio was 0.05.

Synthesis Example 3

Synthesis of (4-n-pentylcyclohexyl)benzene
(Cis/Trans Molar Ratio: 0.02)

In a 2,000 mL (inside volume) three-necked flask equipped with a reflux condenser, 700 mL of anhydrous tetrahydrofuran (THF) and 27 g of magnesium shavings were charged, to which 160 g of bromobenzene were added dropwise at a speed to ensure continuous mild reflux. After the dropping was completed, the mixture was further stirred for 1 h. To this mixture, a solution of 170 g of 4-n-pentylcyclohexanone (available from Tokyo Chemical Industry Co., Ltd.) in 100 mL of THF was added at 50° C. The mixture was then refluxed for 2 h. The obtained reaction product liquid was cooled to room temperature, poured into an aqueous ammonium chloride solution and then extracted with benzene. The benzene solution was added with 1 g of p-toluenesulfonic acid and refluxed while removing water generated. When water was no longer distilled, the reaction mixture was cooled to room temperature, washed with an aqueous sodium hydrogen carbonate solution and then with brine, dried and then concentrated. The residue was purified by silica gel column chromatography to obtain (4-n-pentylcyclohexenyl)benzene. The thus obtained product was dissolved in 1,000 mL of ethyl acetate and subjected to hydrogenation at 0.5 MPa using 2 g of 5% by mass-Pd/C as a catalyst. When a theoretical amount of hydrogen was consumed, the catalyst was separated by filtration. The resulting filtrate was concentrated to obtain 220 g of (4-n-pentylcyclohexyl)benzene. As a result of gas chromatographic analysis, it was confirmed that the (4-n-pentylcyclohexyl)benzene purity was 97.8% and the cis/trans molar ratio was 0.67. In 100 g of hexane were dissolved 220 g of (4-n-pentylcyclohexyl)benzene. The resulting solution was cooled to −30° C. Precipitated crystals were collected by filtration in an amount of 100 g. As a result of analyzing the obtained crystals by gas chromatography, it was confirmed that the (4-n-pentylcyclohexyl)benzene purity was 98.0% and the cis/trans molar ratio was 0.02.

Synthesis Example 4

Synthesis of (trans-4-n-pentylcyclohexyl)benzene

In 50 g of hexane were dissolved 100 g of the (4-n-pentylcyclohexyl)benzene obtained in Synthesis Example 3. The resulting solution was cooled to −30° C. Precipitated crystals were collected by filtration in an amount of 85 g. As a result of analyzing the obtained crystals by gas chromatography, it was confirmed that the product was high purity (trans-4-n-pentylcyclohexyl)benzene having a cis isomer content of 0.8% (cis/trans molar ratio: 0.008).

Synthesis Example 5

Synthesis of (4-n-pentylcyclohexyl)benzene
(Cis/Trans Molar Ratio: 0.67)

In a 2,000 mL (inside volume) three-necked flask equipped with a reflux condenser, 700 mL of anhydrous THF and 27 g of magnesium shavings were charged, to which 160 g of bromobenzene were added dropwise at a speed to ensure continuous mild reflux. After the dropping was completed, the mixture was further stirred for 1 h. To the mixture, a solution of 170 g of 4-n-pentylcyclohexanone (available from Tokyo Chemical Industry Co., Ltd.) in 100 mL of THF was added at 50° C. The mixture was then refluxed for 2 h. The obtained reaction product liquid was cooled to room temperature, poured into an aqueous ammonium chloride solution and then extracted with benzene. The benzene solution was added with 1 g of p-toluenesulfonic acid and refluxed while removing water generated. When water was no longer distilled, the reaction mixture was cooled to room temperature, washed with an aqueous sodium hydrogen carbonate solution and then with an aqueous sodium chloride solution, dried and then concentrated. The residue was purified by silica gel column chromatography to obtain (4-n-pentylcyclohexenyl)benzene. The thus obtained product was dissolved in 1,000 mL of ethyl acetate and subjected to hydrogenation at 0.5 MPa using 2 g of 5% by mass-Pd/C as a catalyst. When a theoretical amount of hydrogen was consumed, the catalyst was separated by filtration. The resulting filtrate was concentrated to obtain 220 g of (4-n-pentylcyclohexyl)benzene. As a result of gas chromatographic analysis, it was confirmed that the (4-n-pentylcyclohexyl)benzene purity was 99.2% and the cis/trans molar ratio was 0.67.

Example 1

In a 500 mL (inside volume) autoclave (made of SUS316L) which was equipped with an electromagnetic stirrer and whose temperature was controllable, 74.3 g (3.71 moles) of anhydrous HF and 50.5 g (0.744 mole) of $BF_3$ were charged. While the contents were stirred and maintained at a liquid temperature of −30° C., the pressure was increased to 2 MPa using carbon monoxide. Then, while maintaining the pressure at 2 MPa and the temperature at −30° C., a raw material composed of a mixture of 50.0 g (0.248 mole) of (trans-4-n-propylcyclohexyl)benzene (available from Kanto Chemical Co., Inc.; purity: 98% or higher) and 50.0 g of n-heptane was fed to the autoclave and maintained as such for 1 h. The contents in the autoclave were then poured onto ice, diluted with benzene and subjected to a neutralization treatment to obtain an oil layer. The oil layer was analyzed by gas chromatography for determining the results. It was confirmed that the conversion of (trans-4-n-propylcyclohexyl)benzene was 100% and the selectivity to 4-(trans-4-n-propylcyclohexyl)benzaldehyde was 95.2%. The end product was isolated by simple distillation and analyzed by GC-MS. As a result, it was confirmed that the end product had a molecular weight of 230 for 4-(trans-4-n-propylcyclohexyl)benzaldehyde as aimed. The chemical shifts (δ ppm, TMS standard) in $^1$H-NMR in deuterated chloroform were: 0.9 (t, 3H), 1.0-1.6 (m, 9H), 1.9 (m, 4H), 2.55 (m, 1H), 7.36 (d, 2H), 7.8 (d, 2H) and 10 (s, 1H). The 4-(4-n-propylcyclohexyl)benzaldehyde purity was 98.3% and the trans isomer purity was 99.0%.

Example 2

A formylation reaction and a treatment of the reaction liquid were carried out in the same manner as those in Example 1 except that a mixture of 53.6 g (0.248 mole) of (trans-4-n-butylcyclohexyl)benzene (available from Kanto Chemical Co., Inc.; purity: 98% or higher) and 53.6 g of n-heptane was charged as a raw material. The obtained oil layer was analyzed by gas chromatography for determining the results. It was confirmed that the conversion of (trans-4-n-butylcyclohexyl)benzene was 100% and the selectivity to 4-(trans-4-n-butylcyclohexyl)benzaldehyde was 94.5%. The end product was isolated by simple distillation and analyzed by GC-MS. As a result, it was confirmed that the end product had a molecular weight of 244 for 4-(trans-4-n-butylcyclohexyl)benzaldehyde as aimed. The chemical shifts ($\delta$ ppm, TMS standard) in $^1$H-NMR in deuterated chloroform were: 0.91 (t, 3H), 1.03 (q, 2H), 1.2-1.3 (m, 7H), 1.47 (q, 2H), 1.89 (d, 4H), 2.55 (t, 1H), 7.36 (d, 2H), 7.80 (d, 2H) and 9.96 (s, 1H). The 4-(trans-4-n-butylcyclohexyl)benzaldehyde purity was 98.5% and the trans isomer purity was 99.2%.

Example 3

A formylation reaction and a treatment of the reaction liquid were carried out in the same manner as those in Example 1 except that a mixture of 57.0 g (0.248 mole) of (trans-4-n-pentylcyclohexyl)benzene obtained in Synthesis Example 4 and 57.0 g of n-heptane was charged as a raw material. The obtained oil layer was analyzed by gas chromatography for determining the results. It was confirmed that the conversion of (trans-4-n-pentylcyclohexyl)benzene was 100% and the selectivity to 4-(trans-4-n-pentylcyclohexyl)benzaldehyde was 96.2%. The trans isomer purity was 99.999% and the cis isomer purity was 10 ppm.

Example 4

In a 500 mL (inside volume) autoclave (made of SUS316L) which was equipped with an electromagnetic stirrer and whose temperature was controllable, 74.3 g (3.71 moles) of anhydrous HF and 50.5 g (0.744 mole) of $BF_3$ were charged. While the contents in the autoclave were stirred and maintained at a liquid temperature of −30° C., the pressure was increased to 2 MPa using carbon monoxide. Then, while maintaining the pressure at 2 MPa and the temperature at −30° C., a raw material composed of a mixture of 50.0 g (0.248 mole; cis/trans molar ratio: 0.05) of (4-n-propylcyclohexyl)benzene [[4-(4-n-propylcyclohexyl)benzene]] obtained in Synthesis Example 2 and 50.0 g of n-heptane was fed to the autoclave and maintained as such for 1 h. The contents in the autoclave were then poured onto ice, diluted with benzene and subjected to a neutralization treatment to obtain an oil layer. The oil layer was analyzed by gas chromatography for determining the results. It was confirmed that the conversion of (4-n-propylcyclohexyl)benzene [[4-(4-n-propylcyclohexyl)benzene]] was 100% and the selectivity to 4-(trans-4-n-propylcyclohexyl)benzaldehyde was 95.2%. The trans isomer purity was 99.997% and the cis isomer purity was 26 ppm.

Example 5

Formylation

A 10 L (inside volume) autoclave (made of stainless steel) which was equipped with a magnet drive stirrer, three upper inlet nozzles, one bottom outlet nozzle and a jacket for controlling the inside temperature was used. The atmosphere in the autoclave was replaced with carbon monoxide. Then, the autoclave was charged with 1,793 g (89.6 moles) of HF and 1,215 g (17.9 moles) of BF3. While the contents were stirred and maintained at a liquid temperature of −30° C., the pressure was increased to 2 MPa using carbon monoxide. Then, while maintaining the pressure at 2 MPa and the temperature at −30° C., a raw material composed of a mixture of 1,209 g (6.0 moles; cis/trans molar ratio: 0.05) of (4-n-propylcyclohexyl)benzene [[4-(4-n-propylcyclohexyl)benzene]] obtained in Synthesis Example 2 and 1,209 g of n-heptane was fed to the autoclave from an upper portion thereof over about 90 min to perform formylation. The stirring was then continued for about 20 min until carbon monoxide was no longer absorbed. In this case, the amount of carbon monoxide absorbed was 5.9 moles.

A part of the obtained reaction liquid was sampled in ice water, diluted with benzene and then subjected to a neutralization treatment to obtain an oil layer. The oil layer was analyzed by gas chromatography for determining the results. It was confirmed that the conversion of (4-n-propylcyclohexyl)benzene [[4-(4-n-propylcyclohexyl)benzene]] was 96.8% and the selectivity to 4-(trans-4-n-propylcyclohexyl)benzaldehyde was 90.0%.

Thermal Decomposition of Complex:

A distillation tower having an inside diameter of 76 cm and a length of 176 cm and packed with Rachig rings made of TEFLON (registered trademark) was used for decomposing an HF/$BF_3$/4-(trans-4-n-propylcyclohexyl)benzaldehyde complex. A solution of the complex was fed to an intermediate portion of the distillation tower at a rate of 410 g/h, while benzene as a decomposition aid was fed to a lower portion of the distillation tower at a rate of 500 g/h. The inside pressure of the tower was 0.4 MPa, the tower bottom temperature was 140° C. and the tower bottom liquid was withdrawn at a rate of 544 g/h. From a top of the tower were withdrawn HF and $BF_3$ used as a catalyst, while 4-(trans-4-n-propylcyclohexyl)benzaldehyde was discharged from the tower bottom together with a large amount of benzene. It was confirmed that an inorganic fluorine content relative to 4-(trans-4-n-propylcyclohexyl)benzaldehyde in the tower bottom was 221 ppm and the complex decomposition efficiency was 99.9%. The 4-(trans-4-n-propylcyclohexyl)benzaldehyde purity was 90.5%.

Purification by Distillation:

The tower bottom liquid obtained from the complex was neutralized with a 2% by mass aqueous NaOH solution, washed with water and then distilled using a rectification tower having 20 theoretical plates to obtain, as a main fraction, 1,218.7 g of 4-(trans-4-n-propylcyclohexyl)benzaldehyde having a purity of 98.7%. The trans isomer purity was 99.993% and the cis isomer purity was 73 ppm.

Example 6

A formylation reaction and a treatment of the reaction liquid were carried out in the same manner as those in Example 1 except that a mixture of 57.0 g (0.248 mole, cis/trans molar ratio: 0.02) of (4-n-pentylcyclohexyl)benzene [[4-(4-n-pentylcyclohexyl)benzene]] obtained in Synthesis Example 3 and 57.0 g of n-heptane was charged as a raw material. The obtained oil layer was analyzed by gas chromatography for determining the results. It was confirmed that the conversion of (4-n-pentylcyclohexyl)benzene [[4-(4-n-pentylcyclohexyl)benzene]] was 100% and the selectivity to 4-(trans-4-n-pentylcyclohexyl)benzaldehyde was 96.2%. The trans isomer purity was 99.997% and the cis isomer purity was 25 ppm.

Example 7

A formylation reaction and a treatment of the reaction liquid were carried out in the same manner as those in Example 1 except that a mixture of 50.0 g (0.248 mole, cis/trans molar ratio: 0.10) of (4-n-propylcyclohexyl)benzene [[4-(4-n-propylcyclohexyl)benzene]] and 50.0 g of n-heptane was charged as a raw material. The obtained oil layer was analyzed by gas chromatography for determining the results. It was found that the conversion of (4-n-propylcyclohexyl)benzene [[4-(4-n-propylcyclohexyl)benzene]] was 100% and the selectivity to 4-(trans-4-n-propylcyclohexyl)benzaldehyde was 89.7%. The trans isomer purity was 99.98% and the cis isomer purity was 197 ppm.

Example 8

In a 500 mL (inside volume) autoclave (made of SUS316L) which was equipped with an electromagnetic stirrer and whose temperature was controllable, 74.3 g (3.71 moles) of anhydrous HF and 5.05 g (0.074 mole) of $BF_3$ were charged. While the contents in the autoclave were stirred and maintained at a liquid temperature of −30° C., a raw material composed of a mixture of 50.0 g (0.248 mole; cis/trans molar ratio: 1.36) of (4-n-propylcyclohexyl)benzene obtained in Synthesis Example 1 and 50.0 g of n-heptane was fed to the autoclave and maintained as such for 0.5 h. The contents in the autoclave were then poured onto ice, and subjected to a neutralization treatment to obtain an oil layer. As a result of analyzing the oil layer by gas chromatography, it was confirmed that the (trans-4-n-propylcyclohexyl)benzene purity was 91.0% and the trans cis/trans molar ratio was 0.05.

Example 9

Isomerization

A 10 L (inside volume) autoclave (made of stainless steel) which was equipped with a magnet drive stirrer, three upper inlet nozzles, one bottom outlet nozzle and a jacket for controlling the inside temperature was used. The autoclave was charged with 1,793 g (89.6 moles) of HF and 122.0 g (1.8 moles) of $BF_3$. While the contents in the autoclave were stirred and maintained at a liquid temperature of −30° C., a raw material composed of a mixture of 1,209 g (6.0 moles; cis/trans molar ratio: 1.36) of (4-n-propylcyclohexyl)-benzene obtained in Synthesis Example 1 and 1,209 g of n-heptane was fed to the autoclave from an upper portion thereof over about 90 minutes to perform isomerization. A part of the obtained reaction liquid was sampled in ice water, and subjected to a neutralization treatment to obtain an oil layer. The oil layer was analyzed by gas chromatography for determining the results. It was confirmed that the (trans-4-n-propylcyclohexyl)benzene purity was 92.5% and the cis/trans molar ratio was 0.05.

Thermal Decomposition of Complex:

A distillation tower having an inside diameter of 76 cm and a length of 176 cm and packed with Rachig rings made of TEFLON (registered trademark) was used for decomposing an $HF/BF_3$/(trans-4-n-propylcyclohexyl)benzene complex. A solution of the complex was fed to an intermediate portion of the distillation tower at a rate of 410 g/h, while benzene as a decomposition aid was fed to a lower portion of the distillation tower at a rate of 500 g/h. The inside pressure of the tower was 0.4 MPa, the tower bottom temperature was 140° C. and the tower bottom liquid was withdrawn at a rate of 544 g/h. From a top of the tower were withdrawn HF and $BF_3$ used as a catalyst, while (trans-4-n-propylcyclohexyl)benzene was discharged from the tower bottom together with a large amount of benzene. It was confirmed that an inorganic fluorine content relative to (trans-4-n-propylcyclohexyl)benzene in the tower bottom was 221 ppm and the complex decomposition efficiency was 99.9%. The (trans-4-n-propylcyclohexyl)benzene purity was 95.5%.

Purification by Distillation:

The tower bottom liquid obtained from the complex was neutralized with a 2% by mass aqueous NaOH solution, washed with water and then distilled using a rectification tower having 20 theoretical plates to obtain, as a main fraction, 1,150 g of (trans-4-n-propylcyclohexyl)benzene having a purity of 99.2%.

Example 10

An isomerization reaction and a treatment of the reaction liquid were carried out in the same manner as those in Example 8 except that a mixture of 57.0 g (0.248 mole, cis/trans molar ratio: 0.67) of (4-n-pentylcyclohexyl)benzene obtained in Synthesis Example 5 and 57.0 g of n-heptane was charged as a raw material. The obtained oil layer was analyzed by gas chromatography. As a result, it was confirmed that the (trans-4-n-pentylcyclohexyl)benzene [[(trans-4-n-propylcyclohexyl)benzene]] purity was 90.5% and the cis/trans molar ratio was 0.05.

Incidentally, the gas chromatography in Synthesis Examples 1 to 4 and Examples 1 to 7 was carried out under the following conditions.

A gas chromatograph (GC-17A available from Shimadzu Corporation) and a capillary column (HR-1 available from Shinwa Chemical Industries, Ltd., 0.32 mmϕ×25 m) were used. Temperature conditions included a temperature rise rate of 5° C./min between 100° C. and 300° C.

In Synthesis Example 5 and Examples 8 to 10, the gas chromatography was carried out under the following conditions.

A gas chromatograph (GC-17A available from Shimadzu Corporation) and a capillary column (DB-WAX available from Agilent Technologies, 0.32 mmϕ×30 m) were used. The temperature was maintained at 100° C. for 60 min, then increased from 100° C. to 220° C. at a rate of 5° C./min and held at that temperature for 6 min.

INDUSTRIAL APPLICABILITY

According to the present invention, it is possible to effectively produce a 4-(4-alkylcyclohexyl)benzaldehyde, 4-(cyclohexyl)benzaldehyde, a 4-(trans-4-alkylcyclohexyl)benzaldehyde and a (trans-4-alkylcyclohexyl)benzene useful for electronic material applications inclusive of liquid crystals and for pharmaceutical and agrochemical applications.

The invention claimed is:

1. A process for producing a 4-(4-alkylcyclohexyl)-benzaldehyde or 4-(cyclohexyl)benzaldehyde having a purity of 98% or more, comprising formylating a benzene derivative represented by the following formula (1a) with carbon monoxide in the presence of hydrogen fluoride and boron trifluoride to obtain a 4-(4-alkylcyclohexyl)benzaldehyde represented by the following formula (2) or 4-(cyclohexyl)benzaldehyde,

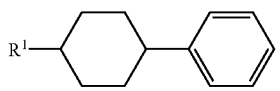

wherein R¹ represents an alkyl group having 1 to 10 carbon atoms, or a hydrogen atom,

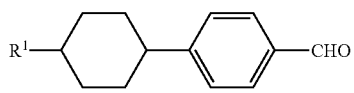

wherein R¹ represents an alkyl group having 1 to 10 carbon atoms, or a hydrogen atom,
wherein the hydrogen fluoride is used in an amount of not less than 2 moles but not more than 20 moles per 1 mole of the benzene derivative represented by the formula (1a),
wherein the boron trifluoride is used in an amount of not less than 1.1 mole but not more than 5 moles per 1 mole of the benzene derivative represented by the formula (1a), and
wherein the formylation is carried out at a temperature of from −50° C. to 30° C.

2. 4-(4-n-Butylcyclohexyl)benzaldehyde represented by the following formula (3) having a 4-(4-n-Butylcyclohexyl) benzaldehyde purity of 98% or more and a trans isomer purity of 99% or more which is produced by the process according to claim 1:

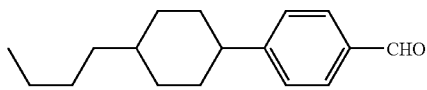

3. A process for producing a 4-(trans-4-alkylcyclohexyl) benzaldehyde having a purity of 98% or more and a trans isomer purity of 99% or more, comprising formylating a (4-alkylcyclohexyl)benzene represented by the following formula (1b) and having a cis/trans molar ratio of 0.3 or less with carbon monoxide in the presence of hydrogen fluoride and boron trifluoride to obtain a 4-(trans-4-alkylcyclohexyl) benzaldehyde represented by the following formula (4),

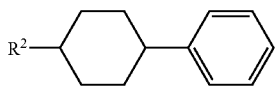

wherein R² represents an alkyl group having 1 to 10 carbon atoms,

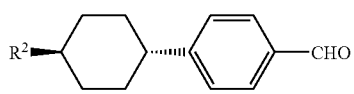

wherein R² represents an alkyl group having 1 to 10 carbon atoms, wherein the hydrogen fluoride is used in an amount of not less than 2 moles but not more than 20 moles per 1 mole of the (4-alkylcyclohexyl)benzene,
wherein the boron trifluoride is used in an amount of not less than 1.1 mole but not more than 5 moles per 1 mole of the (4-alkylcyclohexyl)benzene, and
wherein the formylation is carried out at a temperature of from −50° C. to 30° C.

4. A process for producing a (trans-4-alkylcyclohexyl)benzene represented by the following formula (5), comprising isomerizing a mixture of the cis and trans isomers of a (4-alkylcyclohexyl)benzene represented by the following formula (1b) in the presence of hydrogen fluoride and boron trifluoride,

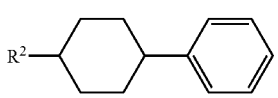

wherein R² represents an alkyl group having 1 to 10 carbon atoms,

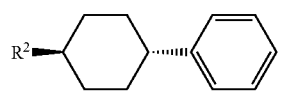

wherein R² represents an alkyl group having 1 to 10 carbon atoms.

5. The process for producing a (trans-4-alkylcyclohexyl) benzene according to claim 4, wherein the hydrogen fluoride is used in an amount of not less than 2 moles but not more than 30 moles per 1 mole of the (4-alkylcyclohexyl)benzene.

6. The process for producing a (trans-4-alkylcyclohexyl) benzene according to claim 4, wherein the boron trifluoride is used in an amount of not less than 0.1 mole but not more than 2 moles per 1 mole of the (4-alkylcyclohexyl)benzene.

7. The process for producing a (trans-4-alkylcyclohexyl) benzene according to claim 4, wherein the isomerization is carried out at a temperature of from −50° C. to 30° C.

8. The process for producing a (trans-4-alkylcyclohexyl) benzene according to claim 4, wherein the (trans-4-alkylcyclohexyl)benzene represented by the following formula (5) has an isomer ratio, in terms of cis/trans molar ratio, of less than 0.1,

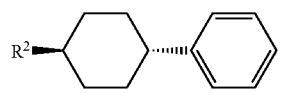

wherein R² represents an alkyl group having 1 to 10 carbon atoms.

9. A process for producing a 4-(trans-4-alkylcyclohexyl) benzaldehyde, comprising isomerizing a mixture of the cis and trans isomers of a (4-alkylcyclohexyl)benzene represented by the following formula (1b) in the presence of hydrogen fluoride and boron trifluoride to obtain a (trans-4-alkylcyclohexyl)benzene represented by the following formula (5), and then, continuedly, formylating the (trans-4-alkylcyclohexyl)benzene with carbon monoxide to obtain a 4-(trans-4-alkylcyclohexyl)benzaldehyde represented by the following formula (4),

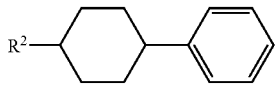
(1b)

wherein $R^2$ represents an alkyl group having 1 to 10 carbon atoms,

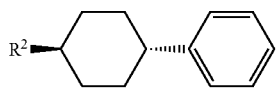
(5)

wherein $R^2$ represents an alkyl group having 1 to 10 carbon atoms,

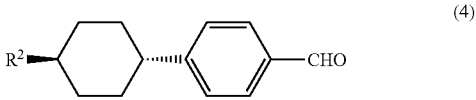
(4)

wherein $R^2$ represents an alkyl group having 1 to 10 carbon atoms.

10. The process for producing a (trans-4-alkylcyclohexyl)benzene according to claim 4, wherein the (4-alkylcyclohexyl)benzene represented by said formula (1b) has an isomer ratio, in terms of cis/trans molar ratio, of 0.3 or less.

11. The process for producing a 4-(trans-4-alkylcyclohexyl)benzaldehyde according to claim 9, wherein the (4-alkylcyclohexyl)benzene represented by said formula (1b), obtained by said isomerizing, has an isomer ratio, in terms of cis/trans molar ratio, of 0.3 or less.

12. The process for producing a 4-(trans-4-alkylcyclohexyl)benzaldehyde according to claim 11, wherein said isomer ratio is 0.1 or less.

* * * * *